United States Patent
Edic et al.

(10) Patent No.: US 6,901,131 B2
(45) Date of Patent: May 31, 2005

(54) METHODS AND APPARATUS FOR COMPUTED TOMOGRAPHY IMAGING

(75) Inventors: Peter Michael Edic, Albany, NY (US); Ahmad Nadeem Ishaque, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 341 days.

(21) Appl. No.: 10/034,133

(22) Filed: Dec. 28, 2001

(65) Prior Publication Data

US 2003/0123604 A1 Jul. 3, 2003

(51) Int. Cl.$^7$ .................................................. A61B 6/00
(52) U.S. Cl. .............................. 378/19; 378/15; 378/4
(58) Field of Search ............................. 378/4, 19, 15, 378/901, 14, 98.8

(56) References Cited

U.S. PATENT DOCUMENTS

| | | | |
|---|---|---|---|
| 4,637,040 A | * 1/1987 | Sohval et al. .................. 378/9 |
| 5,449,913 A | * 9/1995 | Chang .................... 250/363.04 |
| 5,541,971 A | 7/1996 | Saito |
| 5,583,903 A | 12/1996 | Saito et al. |
| 5,697,010 A | 12/1997 | Masuda et al. |
| 5,717,732 A | 2/1998 | Tam |
| RE35,848 E | * 7/1998 | Tanaka ......................... 378/16 |
| 5,828,718 A | 10/1998 | Ruth et al. |
| 5,848,117 A | 12/1998 | Urchuk et al. |
| 5,946,371 A | * 8/1999 | Lai .............................. 378/19 |
| 5,991,356 A | 11/1999 | Horiuchi et al. |
| 6,118,841 A | * 9/2000 | Lai .............................. 378/19 |
| 6,185,271 B1 | * 2/2001 | Kinsinger ..................... 378/19 |
| 6,359,956 B1 | * 3/2002 | Hsieh et al. ................... 378/15 |
| 6,366,637 B1 | * 4/2002 | Hsieh et al. ................... 378/19 |

* cited by examiner

*Primary Examiner*—David V. Bruce
*Assistant Examiner*—Irakli Kiknadze
(74) *Attorney, Agent, or Firm*—Fletcher Yoder

(57) ABSTRACT

A method for arranging detector sections for an imaging system that has a field of view that is defined by a rotational axis and imaging geometry is provided. The method includes providing a plurality of detector sections, and arranging the detector sections in an asymmetric arrangement about a central axis of the field of view.

18 Claims, 3 Drawing Sheets

METHODS AND APPARATUS FOR COMPUTED TOMOGRAPHY IMAGING

BACKGROUND OF THE INVENTION

This invention relates generally to methods and apparatus for Computed Tomography (CT) imaging and other radiation imaging systems and, more particularly, to facilitating a reduction of artifacts in reconstructed images.

In at least some CT imaging system configurations, an x-ray source projects a fan-shaped x-ray beam which is collimated to lie within an X-Y plane of a Cartesian coordinate system, generally referred to as an "imaging plane". The x-ray beam passes through an object being imaged, such as a patient. The beam, after being attenuated by the object, impinges upon an array of radiation detectors. The intensity of the attenuated x-ray beam radiation received at a detector array is dependent upon the attenuation of the x-ray beam by the object. Each detector element of the array produces a separate electrical signal that is a measurement of the x-ray intensity signal, facilitating computation of the beam attenuation, at the detector location. The intensity measurements from all of the detectors are acquired separately and are used to compute a profile of the line integral of the linear attenuation coefficient of the object, which is denoted as projection data. Volumetric CT imaging systems have source collimation such that a cone-shaped beam of x-rays illuminate the patient to be imaged and an area detector is used to measure the x-ray energy that is not attenuated by the patient, giving rise to a two-dimensional projection image.

In at least some known "third generation" CT systems, the relative orientation of the x-ray source and the detector array are held fixed. The x-ray source and the detector array are then rotated with a gantry within the imaging plane, and around the object to be imaged, so the angle at which the x-ray beam intersects the object changes. X-ray sources typically include x-ray tubes, which emit the x-ray beam from a focal spot. X-ray detectors typically include a collimator for collimating x-ray beams and removing scattered x-rays (x-rays that interact with the patient being imaged and are redirected towards the detector) received at the detector, a scintillator adjacent the collimator, and photodetectors adjacent to the scintillator.

In particular embodiments of a volumetric CT system, area radiation detector arrays may be approximately twenty centimeters (cm) square or less and the array and gantry are rotated 360° about the patient to produce a complete image. Conversely, the x-ray tube and gantry can be held constant (stationary gantry) while the object is rotated during data acquisition. These schemes can be implemented in industrial CT systems, such as, for example, but not limited to, a baggage scanning CT system for an airport or other transportation center. The former CT system topology will be described in detail in the text that follows. However, methods described herein are equally applicable to stationary gantry systems and are not meant to limit the scope of the invention. Additionally, in the text that follows, the term "detector sections" refers to both linear radiation detectors and area radiation detectors.

Although the collection of projection images as proposed above is not mathematically complete when the embodiment includes area radiation detectors, it is possible to reconstruct a volumetric or three-dimensional (3-D) representation of the object from the measured data. Moreover, to acquire enough data for diagnostic image quality, the shadow of the patient on the detector, resulting from x-ray illumination of the patient, must not extend past the edge of the detector. Considering typical magnification in a CT system and a particular embodiment of a CT system utilizing a 20-cm square area detector, this requires that the diameter of the patient be approximately 13 cm or less. One known solution to increase the field of view of the imaging system involves using two or more digital radiation detector arrays that are butted together. However, such detector arrays generally have areas or zones in which the x-rays are not detected in the region where the detectors butt. These zones are commonly referred to as dead zones. Because x-ray projection data is not acquired in the dead zones, the missing projection data caused by the dead zones may produce artifacts in the reconstructed images of the 3-D volume of the scanned object.

BRIEF SUMMARY OF THE INVENTION

In one aspect, a method for arranging detector sections for an imaging system that has a field of view that is defined by a rotational axis and imaging geometry is provided. The method includes providing a plurality of detector sections, and arranging the detector sections in an asymmetric arrangement about a central axis of the field of view.

In another aspect, a method for arranging detector sections for an imaging system that has a field of view that is defined by a rotational axis and imaging geometry is provided. The method includes providing a plurality of detector sections that have substantially equal lengths, and positioning adjacent detector sections at a distance apart that is less than the length of the detector sections. The method also includes arranging the detector sections in an asymmetric arrangement about a central axis of the field of view such that at least one of the detector sections is proximate to an edge of the field of view.

In a further aspect, a detection array for an imaging system that has a field of view that is defined by a rotational axis and imaging geometry is provided. The array includes a plurality of detector sections arranged asymmetric about a central axis of the field of view.

In another aspect, a detection array for an imaging system that has a field of view that is defined by a rotational axis and imaging geometry is provided. The detection array includes a plurality of detector sections that have substantially equal lengths. Adjacent detector sections are a distance apart that is less than the length of the detector sections. The detector sections are arranged asymmetric about a central axis of the field of view such that at least one of the detector sections is proximate to an edge of the field of view.

In one aspect, a method for performing a computed tomography scan utilizing an imaging system including a gantry and a rotational axis that defines a field of view is provided. The method includes providing a plurality of detector sections, and arranging the detector sections in an asymmetric arrangement about a central axis of the field of view. The method also includes collecting data from the detector sections in a first position, and rotating the gantry a first angular increment and subsequent increments to alternate positions such that a plurality of specific angular locations are identified during one complete rotation of the x-ray source about an object. The method also includes collecting data from the detector sections in each position, and using a reconstruction algorithm to generate a reconstruction of the object using the collected data.

In another aspect, a scanning apparatus includes a gantry and an emitter that has a field of view that is defined by a rotational axis and imaging geometry. The emitter is secured to the gantry. The scanning apparatus also includes an array of detector sections secured to the gantry opposite the emitter. The detector sections are arranged asymmetric about a central axis of the field of view.

In a further aspect, a scanning apparatus includes a gantry, and an emitter that has a field of view that is defined by a rotational axis and the imaging geometry. The emitter is secured to the gantry. The scanning apparatus also includes an array of detector sections secured to the gantry opposite the emitter. The detector sections are arranged asymmetric about a central axis of the field of view, and the detector sections have substantially equal lengths. The detector sections are separated by a length that is less that the length of each individual detector sections. The scanning apparatus also includes a processor operationally coupled to the gantry. The processor is configured to collect data from the detector sections in a plurality of gantry positions.

DETAILED DESCRIPTION OF THE INVENTION

Figure 1:
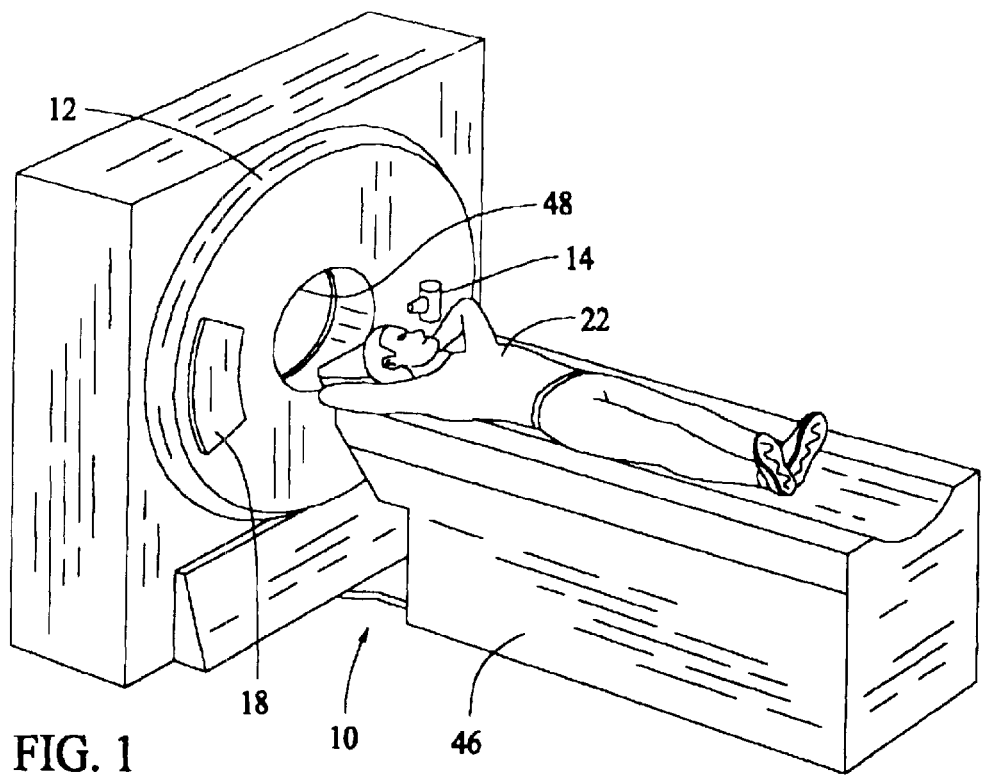
FIG. 1 is a pictorial view of a CT imaging system.
Figure 2:
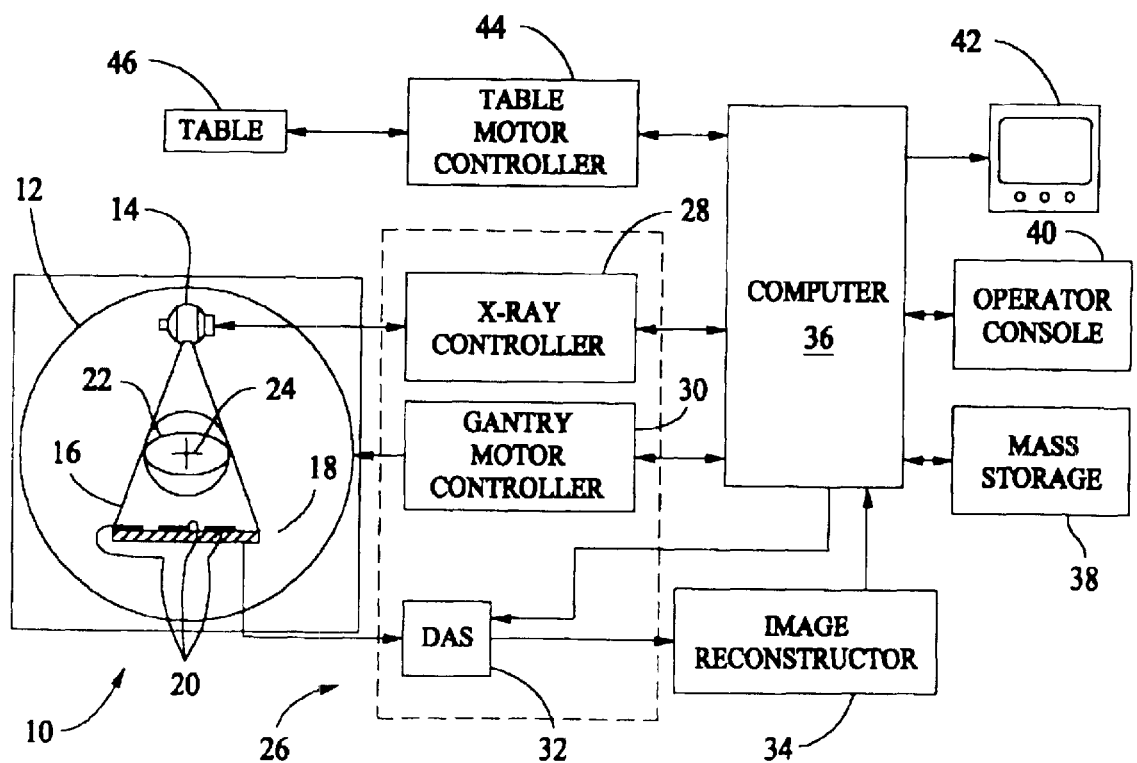
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 (shown in FIG. 2) toward a detector array 18 on the opposite side of gantry 12. The relative orientation of the x-ray source 14 and detector array 18 remains fixed. Referring to FIG. 2, detector array 18 is formed by detector sections 20, which together sense the projected x-rays that pass through an object (ignoring the scatter component of the x-ray intensity), such as a medical patient 22. Each detector section 20 includes a plurality of detector elements (not shown) that each produces an electrical signal that represents the intensity of an impinging x-ray beam on the detector elements. This data can be used to estimate the attenuation of the beam as it passes through patient 22 facilitating generation of the line integrals of the linear attenuation coefficient within object 22 and denoted as projection data. During a scan to acquire x-ray projection data, gantry 12 and the components mounted thereon rotate about a center of rotation 24. In one embodiment, and as shown in FIG. 2, detector sections 20 are arranged in one row so that projection data corresponding to a single image slice is acquired during a scan. In another embodiment, detector sections 20 are arranged in a plurality of parallel rows (area detector), so that projection data corresponding to a plurality of parallel slices can be acquired simultaneously during a scan.

Rotation of gantry 12 and the operation of x-ray source 14 are governed by a control mechanism 26 of CT system 10. Control mechanism 26 may be a separate enclosure housing the subsystems or it may be a collection of individual units, possibly resident on the rotating gantry. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector sections 20 and converts the data to digital signals for subsequent processing. An image reconstructor 34 receives sampled and digitized x-ray data from DAS 32 and performs high-speed image reconstruction. The reconstructed image is applied as an input to a computer 36 that stores the image in a mass storage device 38. The image reconstructor 34 may be a separate piece of hardware or in an alternate configuration may be software executing on the processor in computer 36.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 (shown in FIG. 1) to position patient 22 in gantry 12. In a particular embodiment, table motor controller 44 shown in FIG. 2 may be a component of control mechanism 26. Particularly, table 46 moves portions of patient 22 through gantry opening 48 shown in FIG. 1. Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems.

Figure 3:
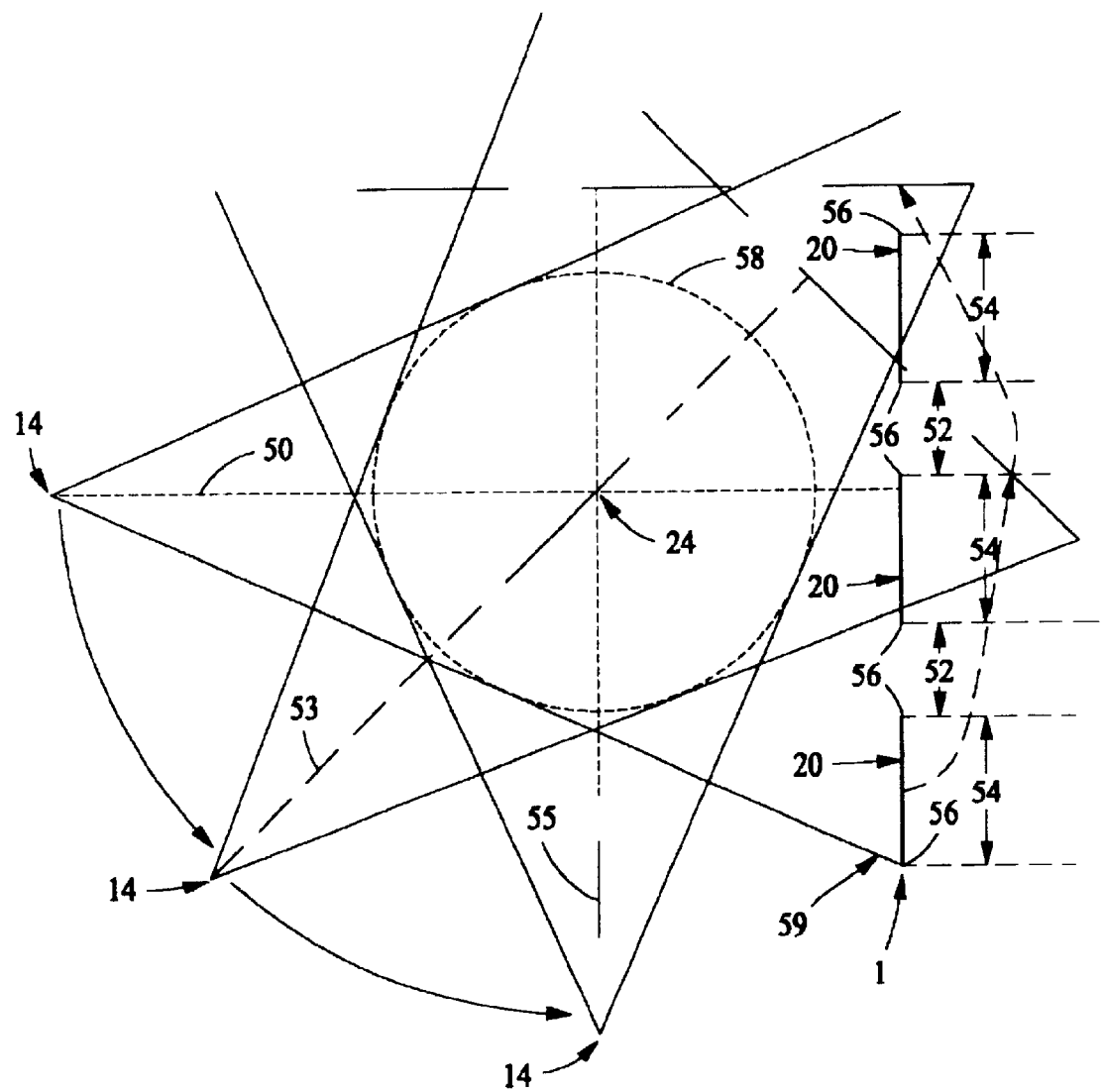
FIG. 3 is another schematic diagram of the CT system illustrated in FIG. 1.

FIG. 3 is another schematic diagram of CT system 10 (shown in FIG. 1). Center of rotation 24 is along a central axis 50 of CT system 10. Patient 22 (shown in FIG. 1) is positioned between x-ray source 14 and detector array 18. Detector array 18 includes a plurality of detector sections 20 spaced apart by a distance 52 (forming gap regions). Detector sections 20 each include a length 54 and a plurality of end portions 56. In one embodiment, distance 52 is less than length 54, and as gantry 12 rotates x-ray source 14 and detector array 18 about patient 22 (shown in FIG. 1), an overlap occurs in end portions 56. For example, in one embodiment, length 54 is approximately twenty centimeters and distance 52 is approximately eighteen centimeters. X-ray source 14 emits radiation forming a field of view that is defined by the rotational axis and imaging geometry. For example, in one embodiment, X-ray source 14 emits radiation in a cone shape forming a field of view 58 in a horizontal cross section whose centerline defines central axis 50. In another embodiment, X-ray source 14 emits radiation in a shape other than a cone shape and forms a field of view in a horizontal cross section whose centerline defines a central axis. Detector sections 20 are arranged in a configuration that is asymmetric about central axis 50. At least one detector section 20 is proximate to an edge 59 of field of view 58. In an alternative embodiment, x-ray source 14 is an emitter that emits radiation including x-rays and radiation other than x-rays.

In use, data is collected and gantry 12 (shown in FIG. 1) is rotated a small angular increment for each subsequent data collection. For example, data is collected while the CT system is positioned along central axis 50 as shown in FIG. 3 for a first data collection, along central axis 53 for a subsequent data collection, and along central axis 55 for yet another collection, etc. Gantry 12 (shown in FIG. 1) is rotated as is usually done in a standard data acquisition sequence for CT imaging. In the embodiment shown in FIG. 3, there are three detector sections 20 each having a length of approximately twenty centimeters, and sections 20 are separated from each other by a distance which is less that 20 centimeters, and are asymmetrically configured. Projection data in the gap regions 52 are measured from subsequent angular positions of the gantry 12 (shown in FIG. 1). These data can be used to reduce artifacts in reconstructed images. Furthermore, since gap regions 52 are less than length 54 of detector sections 20, there are no seam regions that arise from butted detector sections.

Figure 4:
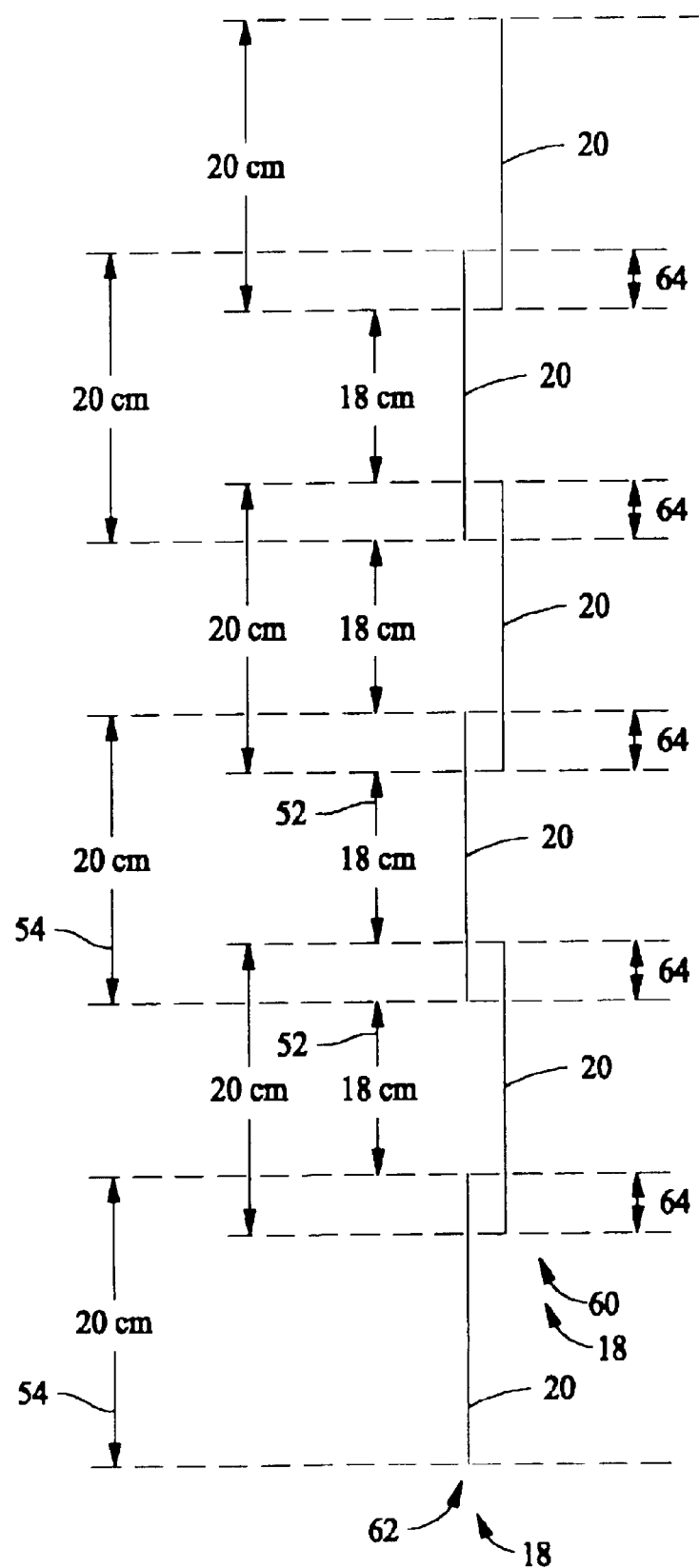
FIG. 4 illustrates a rotation of the detector array shown in FIG. 1.

FIG. 4 illustrates a rotation of detector array 18 (attendant rotational effects are not illustrated for clarity i.e., the rotation appears and is illustrated as a linear motion corresponding to a rotation of 180°). Initially, detector array 18 is in a first position 60 and is rotated 180° (conjugate view position) relative to the first position to an alternate position 62 creating a plurality of one centimeter overlaps 64 between the position of detector sections 20 in first position 60 and the position of detector sections 20 in alternate position 62. As can be seen in FIG. 4, since the spacing of detector sections 20 is less than the length of detector element 20, there is overlap of detector sections 20 in the conjugate view positions. Projection data acquired for a full 360° scan of the patient can be used to reduce artifacts in reconstructed images.

Although described in the context of detector sections 20 with a length 54 of approximately twenty centimeters, and spaced apart by a distance 52 of approximately eighteen centimeters, in other embodiments, detector sections 20 have a length 54 greater than and less than approximately twenty centimeters, and are spaced apart by a distance 52 of less than and more than approximately eighteen centimeters. In addition, the distance 52 between detector sections does not have to be equal for all such gaps. However, to facilitate a reduction in artifacts, in one embodiment, distance 52 is less than length 54. Additionally, overlaps 64 may be less than or more than one centimeter. Accordingly, the benefits of the present invention accrue to all image systems 10 shown in FIG. 1 having a plurality of detector sections 20 positioned in an arrangement that is asymmetric about central axis 50 shown in FIG. 3. Because detector sections 20 in FIG. 4 form overlaps 64 during rotation of gantry 12 in FIG. 2, system 10 acquires a portion of the missing data in distances 52 on alternate locations of the gantry during the scanning of the patient, facilitating recombination of the acquired data for performing a 3-D reconstruction of a volume of patient 22. Additionally, because there are no dead zones, artifacts in the reconstructed 3-D volume are reduced over imaging systems that have dead zones.

While the invention has been described in terms of various specific embodiments, those skilled in the art will recognize that the invention can be practiced with modification within the spirit and scope of the claims.

What is claimed is:

1. A method for arranging detector sections for an imaging system that has a field of view that is defined by a rotational axis and imaging geometry, said method comprising:
providing a plurality of detector sections;
arranging the detector sections in an asymmetric, spaced-apart arrangement about a central axis of the field of view.

2. A method in accordance with claim 1 wherein providing a plurality of detector sections comprises providing a plurality of detector sections that have substantially equal lengths.

3. A method in accordance with claim 2 further comprising positioning adjacent detector sections apart from each other a distance that is less than the length of the detector sections.

4. A method in accordance with claim 3 further comprising positioning at least one of the detector sections proximate to an edge of the field of view.

5. A method in accordance with claim 1 further comprising positioning at least one of the detector sections proximate to an edge of the field of view.

6. A method for arranging detector sections for an imaging system that has a field of view that is defined by a rotational axis and imaging geometry, said method comprising:
providing a plurality of detector sections that have substantially equal lengths;
positioning adjacent detector sections at a distance apart that is less than the length of the detector sections; and
arranging the detector sections in an asymmetric arrangement about a central axis of the field of view such that at least one of the detector sections is proximate to an edge of the field of view.

7. A detection array for an imaging system that has a field of view that is defined by a rotational axis and imaging geometry, said array comprising a plurality of detector sections arranged asymmetrically and spaced-apart about a central axis of the field of view.

8. A detection array in accordance with claim 7 wherein said detector sections have substantially equal length.

9. A detection array in accordance with claim 8 wherein adjacent said detector sections are at a distance apart that is less than said length of said detector sections.

10. A detection array in accordance with claim 9 wherein at least one of said detector sections is proximate to an edge of the field of view.

11. A detection array in accordance with claim 7 wherein at least one of said detector sections is proximate to an edge of the field of view.

12. A detection array for an imaging system that has a field of view that is defined by a rotational axis and imaging geometry, said detection array comprising a plurality of detector sections having substantially equal lengths, adjacent said detector sections are a distance apart that is less than said length of said detector sections, said detector sections arranged asymmetric about a central axis of the field of view such that at least one of said detector sections is proximate to an edge of the field of view.

13. A method for performing a computed tomography scan of an object utilizing an imaging system including a gantry and a rotational axis and imaging geometry that defines a field of view, said method comprising:
providing a plurality of detector sections;
arranging the detector sections in an asymmetric, spaced-apart arrangement about a central axis of the field of view;
collecting data from the detector sections in a first position;
rotating the gantry a first angular increment and subsequent increments to alternate positions such that a plurality of specific angular locations are identified during one complete rotation of an x-ray source and detector about the object;
collecting data from the detector sections in a plurality of angular positions; and
using a reconstruction algorithm to generate a reconstruction of the object using the collected data.

14. A method in accordance with claim 13 wherein said providing a plurality of detector sections further comprises providing a plurality of detector sections that have substantially equal lengths.

15. A method in accordance with claim 14 wherein said collecting data from the detector sections at a plurality of angular positions comprises collecting data from the detector section at each position.

16. A scanning apparatus comprising:
    a gantry;
    an emitter that has a field of view that is defined by a rotational axis and imaging geometry, said emitter secured to said gantry; and
    an array of detector sections secured to said gantry opposite said emitter, said detector sections arranged spaced-apart and asymmetric about a central axis of the field of view.

17. A scanning apparatus in accordance with claim 16 further comprising:
    a processor operationally coupled to said gantry, said processor configured to collect data from said detector sections in at least one of a plurality of positions.

18. A scanning apparatus comprising:
    a gantry;
    an emitter that has a field of view that is defined by a rotational axis and imaging geometry, said emitter secured to said gantry;
    an array of detector sections secured to said gantry opposite said emitter, said detector sections arranged asymmetric about a central axis of the field of view, said detector sections having substantially equal lengths, said detector sections separated by a length that is less that the length of each said individual detector sections; and
    a processor operationally coupled to said gantry, said processor configured to collect data from said detector sections in at least one of a plurality of positions.

* * * * *